United States Patent [19]

Jones et al.

[11] 4,144,271

[45] Mar. 13, 1979

[54] N-SUBSTITUTED MERCAPTOACETAMIDINES AND THEIR USE

[75] Inventors: Howard Jones, Holmdel; Conrad P. Dorn, Plainfield, both of N.J.

[73] Assignee: Merck & Co., Inc., Rahway, N.J.

[21] Appl. No.: 845,096

[22] Filed: Oct. 25, 1977

[51] Int. Cl.$^2$ .......................................... C07C 123/00
[52] U.S. Cl. ............................... 260/564 R; 546/112; 260/239 BA; 544/159; 544/124; 544/85; 260/501.14; 424/244; 424/267; 424/248.52; 424/248.5; 424/326; 542/416
[58] Field of Search .................................... 260/564 R

[56] References Cited

U.S. PATENT DOCUMENTS

| | | | |
|---|---|---|---|
| 3,732,305 | 5/1973 | Bauer | 260/564 R |
| 3,775,478 | 11/1973 | Bockstahler | 260/564 R |

OTHER PUBLICATIONS

Journal of Medicinal Chemistry, vol. 15, pp. 1313–1321 (1972) (Bauer et al.).
Bauer et al., Journal of Medicinal Chemistry, vol. 7, pp. 766–768 (1964).
Conway et al., Journal of Pharmaceutical Science, vol. 57, pp. 455–459 (1968).
Bauer et al., J. Organic Chemistry, vol. 27, pp. 4382–4385 (1962).
Parulkar et al., J. Heterocyclic Chem. (1966), pp. 472–475.

*Primary Examiner*—Gerald A. Schwartz
*Attorney, Agent, or Firm*—Raymond M. Speer; Mario A. Monaco

[57] ABSTRACT

N-substituted mercaptomethylacetamidines are prepared, and are useful as immunoregulants for correcting an imbalance of immune homeostasis, particularly, as immunostimulants in the treatment of autoimmune and immune deficient diseases and disorders.

8 Claims, No Drawings

N-SUBSTITUTED MERCAPTOACETAMIDINES AND THEIR USE

BACKGROUND OF THE INVENTION

Presently, levamisole, (S)-(−)-2,3,5,6-tetrahydro-6-phenylimidazo-[2,1-b]thiazole hydrochloride, is one of the few immunoregulants, or immunepotentiators, in the clinical literature. The clinical efficacy of levamisole in correcting an imbalance of immune homeostasis, and thus its effectiveness in treatment of a number of diseases and disorders characterized or complicated by an imbalance of immune homeostasis, has been confirmed by well-controlled multi-center clinical studies in several diseases and disorders. Consequently, compounds possessing therapeutic properties similar to or better than levamisole would be a valuable contribution to medicine in the field of immunology, or other fields as well. Accordingly, it is an important discovery that the N-substituted mercaptomethylacetamidines of the present invention possess immunological properties similar but superior to those of levamisole, and that they are thus of value in correcting an imbalance of immune homeostasis and for treatment of a number of diseases and disorders characterized or complicated by such an imbalance of immune homeostasis.

SUMMARY OF THE INVENTION

The present invention is concerned with N-substituted mercaptomethylacetamidines, methods for their preparation, a method of correcting an imbalance of immune homeostasis with the compounds, and pharmaceutical compositions containing the compounds as active ingredients.

Particularly, the present invention is concerned with novel compounds of structural formula:

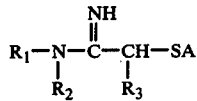

wherein, $R_1$ is aryl, for example, indanyl; haloaryl, for example, chlorophenyl; aralkyl, for example, bicyclo[3,3,1]nonylmethyl, 1-(p-chlorphenyl)benzyl, 1,2-diphenylethyl, 2,2-diphenylethyl; and aralkenyl, for example, cinnamyl;

$R_2$ is hydrogen or $C_{1-6}$ alkyl, for example, methyl and ethyl;

$R_1$ and $R_2$ taken together with the nitrogen atom are morpholino; or

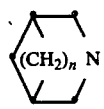

where n is 1 to 3, for example, azabicyclo[3,2,2]

$R_3$ is hydrogen or $C_{1-6}$ alkyl, for example, methyl and ethyl; and

A is hydrogen or

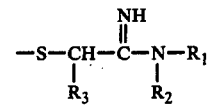

where $R_1$, $R_2$ and $R_3$ are as defined above;
and pharmaceutically acceptable salts thereof, especially the Bunte salts and thiophosphonic acid salts thereof.

Representative novel compounds of the present invention are the following:
N-(m-chlorophenyl)-2-mercaptoacetamidine hydrochloride
N-(2,2-diphenylethyl)-2-mercaptoacetamidine hydrochloride
N-(1-bicyclo-[3,3,1]nonylmethyl)-2-mercaptoacetamidine
N-(1,2-diphenylethyl)-α-mercaptoacetamidine hydrochloride
N-(2-mercaptoacetimidoyl)-3-azabicyclo-[3,2,2]nonane hydrochloride
N-cinnamyl-2-mercaptoacetamidine hydrochloride
N-[1-(p-chlorophenyl)benzyl]-2-mercaptoacetamidine hydrochloride
N-(1-indanyl)-2-mercaptoacetamidine hydrochloride The present invention is also particularly concerned with a method of treatment and compounds for use in correcting an imbalance of immune homeostasis, said compounds having the structural formula:

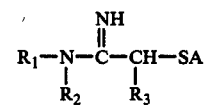

wherein, when $R_3$ is hydrogen, $R_1$ and $R_2$ are the same or different and are independently selected from hydrogen; $C_{1-6}$ alkyl, for example, methyl and ethyl; $C_{1-6}$ cycloalkyl, for example, cyclopentyl; aryl; haloaryl; aralkyl, for example, 1-adamantylmethyl; aralkenyl; and heterocyclic $C_{1-6}$ alkyl, for example, 4-pyridylmethyl; or $R_1$ and $R_2$ taken together with the nitrogen atom are morpholine; or

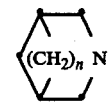

where n is 1 to 3; and
when $R_3$ is $C_{1-6}$ alkyl or aryl, $R_1$ and $R_2$ are hydrogen or $C_{1-6}$ alkyl.

Representative compounds which may be used in correcting an imbalance of immune homeostasis, in addition to those novel compounds enumerated above, are the following:
N-(1-adamantylmethyl)-2-mercaptoacetamidine hydrochloride
2,2'-dithiobis[N-(1-adamantylmethyl)acetamidine]dihydrochloride
N-[2-(1-amadantyl)ethyl]-2-mercaptoacetamidine
2-mercapto-N-4-pyridylmethyl)acetamidine dihydrochloride As already described, the compounds of the present invention are useful in correcting an imbalance of immune homeostasis. Among the diseases and disorders which are characterized or complicated by an imbalance of immune homeostasis are a variety of recurrent and chronic infections and chronic inflammatory conditions. A variety of viral, bacterial, fungal, and protozoal infections may be subject to treatment. The improvement of the potential of certain vaccines and the prevention of viral immunosuppression may also result. A number of primary immune deficiently or autoimmune diseases may be treated, and allergic disorders such as bronchial asthma may be improved. Various rheumatic diseases, including especially rheumatoid arthritis, may be treated. Certain neurologic disorders and gastrointestinal disorders where an imbalance of immune homeostasis plays a role may be improved by treatment. The treatment of some oncologic diseases may be augmented. Particularly, restoration of immune homeostasis following cytostatic treatment or radiotherapy may be improved.

For the purpose of correcting an imbalance of immune homeostasis, the N-substituted mercaptomethylacetamidines of the present invention may be administered orally, topically, parenterally, by inhalation spray, or rectally in dosage unit formulations containing conventional non-toxic pharamceutically acceptable carriers, adjuvants and vehicles. The term parenteral as used herein includes subcutaneous injections, intravenous, intramuscular, intrasternal, intra-articular, injection or infusion techniques. In addition to the treatment of warm-blooded animals such as mice, rats, horses, dogs, cats, etc., the compounds of the present invention are effective in the treatment of humans.

The various forms in which the pharmaceutical compositions containing the active ingredient may be prepared, and the materials and techniques employed in formulating or compounding these various forms, are a matter within the ordinary skill of the artisan.

Dosage levels of the order of 0.1 mg. to 140 mg. per kilogram of body weight per day are useful in correcting an imbalance of immune homeostatis (25 mg. to 7g. per patient per day). For example, diseases and disorders characterized by or complicated by an imbalance of immune homeostasis are effectively treated by the adminsitration of about 0.5 to 50 mg. of the compound per kilogram of body weight per day (5 mg. to 3.5 g. per patient per day). Advantageously, from about 1 mg. to about 15 mg. per kilogram of body weight per daily dosage produces highly effective results (50 mg. to 1 g. per patient per day).

The amount of active ingredient that may be combined with the carrier materials to produce a single dosage form will vary depending upon the host treated and the particular mode of administration. For example, a formulation intennded for the oral administration of humans may contain from 5 mg. to 5 g. of active agent compounded with an appropriate and convenient amount of carrier material which may vary from about 5 to about 95 percent of the total composition. Dosage unit forms will generally contain between from about 25 mg. to about 500 mg. of active ingredient.

It will be understood, however, that the specific dose level for any particular patient will depend upon a variety of factors, including the activity of the specific compound employed, the age, body weight, general health, sox, diet, time of administration, route of administration, rate of excretion, drug combination and the severity of the particular disease undergoing therapy.

In addition to the mercapto or thiol compounds of the present invention described above, there may be employed deliverable or latentiated formms of the mercapto or thiol compounds.

It is well known in the art that the mercapto group is subject to reaction with aldehydes and ketones to form hemimercaptals and hemimercaptoles. It is similarly known in the art, Field et al., *J. Med. Chem.* 12, 624–628 (1969) that many of these hemimercaptals and hemimercaptoles prepared from biologically active mercaptans serve as "latentiating" derivatives, or as chemical modifications of biologically active compounds to form new compounds, which upon in vivo enzymatic or chemical transformation will liberate the parent compounds. Latentiation may also provide means of favorably influencing absorption, transport, distribution, localization, metabolismm, toxicity, and duration of action, as well as stability. Included with the group of aldehydes and ketones suitable for this purpose are chloral, hexafluoroacetone, acetone, benzaldehyde, pyruvate, and ketomalonate. Since latentiation of marcapto groups by this means is known in the art, these latentiating derivatives are considered to be within the spirit and scope of the novel method of treatment and novel compounds of this invention.

Another meams of latentiation is by addition of the thiols of this invention to $\alpha,\beta$-unsaturated acids such as maleic acid and cinnammic acid as described by Srivistava et al., *J. Med. Chem.*, 16, 428–429 (1973).

Latentiation may also be achieved by substitution of the mercapto hydrogen with a 1-methyl-4-nitroimidazol-5-yl group as in azathioprine or a pivaloyloxymethyl group.

The N-substituted mercaptomethylacetamidines of the present invention may be prepared in accordance with the illustrative Examples which follow. Certain of the compounds may also be prepared in accordance with the procedures described in the following literature references: (1) Westland et al., *Journal of Medicinal Chemistry*, Vol. 15, No. 12, pp. 1313–1321 (1972); (2) Bauer and Sandberg, *Journal of Medicinal Chemisitry*, Vol. 7, pp. 766–768 (1964); Consay et al., *Journal of Pharmaceutical Sciences, Vol.* 57, No. 3, pp. 445–459 (March, 1968); and (4) Bauer and Welsh, *Journal of Organic Chemistry*, Vol. 27, pp. 4382–4385 (December, 1962).

EXAMPLE 1

2-Mercapto-N-[endo-2-norboranyl)acetamidine hydrochloride

To a solution of 5.4 g. (0.03 mole) of trisodiumphosphorothioate in water (40 ml.) was added 6.7 g. (0.03 mole) of 2-chloro-N-(endo-2-norbornanyl)acetamidine hydrochloride [*Can. J. Chem.* 47, 1233–1237 (1962)]. The solution was stirred at room temperature for 10 minutes. 30 ml. of 6N HCl was added and the solution heated on a steam bath for 10 minutes under $N_2$. The solution was evaporated to dryness at 40–60° C. under reduced pressure. The product was extracted with isopropanol (35 ml.). The filtered solution was diluted with ether. 5.3 g. of a white solid was recovered by filtration (m.p. 160–165° C.). This solid was recrystallized from isopropanol (m.p. 161.5–164° C.).

EXAMPLE 2

N-(2-indanyl)-2-mercaptoacetamidine hydrochloride

Step A: N-chloroacetimidoyl-2-aminoindane hydrochloride

To a stirred solution of 0.54 g. (0.01 mole) of sodium methoxide in 100 ml. methanol was added 7.6 g. (0.1 mole) chloroacetonitrile with cooling. The solution was stirred at room temperature for 1 ½ hours. Then there was added a solution of 10.9 g. (0.1 mole) of 2-aminoindane in 50 ml. of methanol and 16.66 ml. of 6N ethanolic hydrochloric acid (0.1 mole). The solution was stirred at room temperature for 4 hours and concentrated to dryness at room temperature under high vacuum. The product was recrystallized from isopropanol.

Step B. N-(2-indanyl)-2-mercaptoacetamidine hydrochloride)

The procedures described above in Example 1 were carried out on 4.0 g. (0.0149 mole) of the product of Step A above and 2.68 g. (0.0149mole) of trisodium-phosphorothioate in 25 ml. of water. The product was recrystallized from ethanol: ether [m.p. 102–103° C. (decomposition)].

EXAMPLE 3

N-(1-indanyl)-2-mercaptoacetamidine hydrochloride

The procedures of Example 2 above were followed, substituting 1-aminoindane for the 2-aminoindane of Example 2. As a result, there was produced N-(1-indanoyl)-2-mercaptoacetamidine hydrochloride (m.p. 163–166° C.).

EXAMPLE 4

α-Mercapto-N,N'-dimethylbenzamidinium hydrochloride

Step A: α-Isothiouronium-N,N'-dimethylbenzamidinium dihydrochloride

A suspension of thiourea (3.4 g., 0.005 mole) and α-chloro-N,N'-dimethylbenzamidinium chloride (16.65, 0.05 mole) in tetrahydrofuran (50 ml.) was refluxed for 48 hours. The solid was filtered off and recrystallized from absolute methanol.

Step B: α-Mercapto-N,N'-dimethylbenzamidinium hydrochloride

The above isothiouronium salt (15.45 g., 0.05 mole) was refluxed in 1:1 aqueous ethanol (100 ml.) for 4 hours. The resulting solid was filtered and washed with water. The dried product was dissolved in dry tetrahydrofuran and dry gaseous hydrogen chloride was bubbled in. The product was filtered and recrystallized from ethanol.

EXAMPLE 5

N-(-2-Mercaptoacetamidinyl-3-azabicyclo [3,2,2]nonane hydrochloride

Step A: N-(2-chloroacetamidyl)-3-azabicyclo [3,2,2]nonane hydrochloride

The procedures of Example 2, Step A, described above were followed using the following mmaterials:
7.6 g. (0.1 mole) chloroacetonitrile;
0.54 g. (0.01 mole) sodium methoxide;
12.5 g (0.1 mole) 3-azabicyclo [3,2,2] nonane; and
16.66 ml (0.1 mole) 6N-ethanolic hydrochloric acid There was obtained 12.8 g. of N-(2-chloroacetamidyl)-3-azabicyclo [3,2,2] nonane hydrochloride (m.p. 210–220° C.).

Step B: N-(2-Mercaptoacetamidinyl)-3-azabicyclo [3,2,2]nonane hydrochloride

The procedures of Example 2, Step B, described above were followed using the following materials:

7.1 g. (0.03 mole) of the product from Step A above; and 5.4 g. (0.03 mole) trisodium phosphorothioate There was obtained 4.02 g. of N-(2-mercaptoacetamidinyl)-3-azabicyclo [3,2,2] nonane hydrochloride (m.p. 173–175° C.).

Following the procedures described above, and substituting the particular amines enumerated below, there was obtained the following compounds of the present invention:

| Starting amine | Intermediate chloro-acetamidyl hydrochloride compound | Product mercapto-acetamidine |
|---|---|---|
| Morpholine | 4-(2-chloroacetimidyl)-morpholine hydrochloride (m.p. 162–165° C) | 4-(2-mercapto-acetimidyl)-morpholine hydrochloride (m.p. 147–149° C) |
| Diphenylmethyl amine | N-diphenylmethyl-2-chloroacetamidine hydrochloride (m.p. 234–235° C) | N-diphenylmethyl-2-mercaptoacetamidine hydrochloride (m.p. 225–226.5° C) |
| m-chloroaniline | 3-(N-chloroacetamidine) chlorobenzene hydrochloride | 3-(N-mercapto-acetamidine) chlorobenzene hydrochloride (m.p. 126–128° C) |
| aniline | N-phenyl-2-chloroacet-amidine hydrochloride (m.p. 160–163° C) | N-phenyl-2-mercapto-acetamidine hydrochloride (m.p. 129–132° C) |
| cinnamylamine | N-chloroacetimidoyl-cinnamylamine hydrochloride | N-cinnamyl-2-mercaptoacet-amidine hydrochloride (m.p. 55–60° C: dec.) |
| N-methyl-benzylamine | N-benzyl-N-methyl-2-chloroacetamidine hydrochloride (m.p. 158.5–160.5° C) | N-benzyl-N-methyl-2-mercaptoacet-amidine hydrochloride (m.p. 201.5–203° C) |
| 4-pyridinyl-methylamine | N-(4-pyridinylmethyl)-2-chloroacetamidine di-hydrochloride | N-(4-pyridinyl-methyl)-2-mercap-toacetamidine di-hydrochloride (m.p. 190–194° C) |
| Bicyclo [3,3,1] nonylmethyl amine | N-(1-bicyclo [3,3,1] nonylmethyl)-2-chloro-acetamidine hydrochloride | N-(1-bicyclo [3,3,1]nonylmethyl)-2-mercaptoacet-amidine hydrochloride (m.p. 211–212.5° C) |
| 1,2-diphenyl-ethylamine | N-(1,2-diphenylethyl-α-chloroacetamidine hydrochloride | N-(1,2-diphenyl-ethyl)-α-mercap-toacetamidine hydrochloride (m.p. 187° C) |
| 1-norbornyl-methylamine | 2-chloro-N-(1-norbornyl-methyl)acetamidine hydrochloride | 2-mercapto-N-(1-norbornyl-methyl)acetami-dine hydrochloride (m.p. 135° C) |

EXAMPLE 6

Preparation of Bunte salts 0.1 mole of the 2-chloroacetamidinyl compounds described above in Example 5, Step B, and sodium thiosulfate pentahydrate (0.1 mole) in water (50 ml.) are heated at 100° C. for 1 hour. On cooling in an ice bath, the product crystallizes out, and is collected and purified.

EXAMPLE 7

Preparation of thiophosphonic acid salts

To a stirred solution of 0.02 mole of the 2-chloroacetamidinyl chloride described above in Example 2, Step B, was added trisodium phosphorothioate (*Acta. Chem. Scand.* 14, 1980 (1960), *J. Org. Chem.* 32, 1261 (1967)) (0.02 mole) in water (30 ml.). This solution was stirred for 10 minutes at 25° C. The filtrate was diluted with methanol (50 ml.) and a mixture cooled. The product which crystallized out was collected, dried and purified.

EXAMPLE 8

Preparation of disulfide compounds

The following methods may be employed to prepare the disulfide compounds of the present invention:

Method A: A solution of the Bunte salts prepared as described in Example 6 above (0.06 mole) in 6N hydrochloric acid (250 ml.) are refluxed for 24 hours. The reaction mixture is evaporated in vacuo and the residue recrystallized from isopropanol.

Method B: A solution of the mercaptoacetamidine hydrochlorides described in the Examples above (0.06 mole) in water (100 ml.) are added to an aqueous 30% hydrogenperoxide solution (86 ml. is 1 mole) (0.06 mole) at 0–5° C. over 30 minutes with stirring. The solution is poured into an aqueous saturated sodium bicarbonate solution and th precipitated disulfide filtered off and crystallized to purity.

Method C: The chloracetamidinyl hydrochlorides described in the Examples above (0.1 mole) together with thiourea (0.1 mole) are dissolved in 250 ml. of 99% ethanol and refluxed for 30 minutes. On cooling, the isothiouronium acetamidinyl hydrochloride crystallizes out. This compound is then stirred at 50° with 1N HCl (600 ml.) and then hydrolyzed with 10% aqueous NaOH containing 10% aqueous hydrogen peroxide solution. When the final solution is neutralized with 10% hydrochloric acid solution, the disulfide percipitates out and is collected and purified.

What is claimed is:

1. A compound of structural formula:

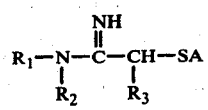

wherein,
$R_1$ is indanyl; chlorophenyl; bicyclo [3,3,1]nonylmethyl, 1-(p-chlorphenyl)benzyl, 1,2-diphenylethyl; or 2,2-diphenylethyl; and cinnamyl;
$R_2$ is hydrogen or $C_{1-6}$ alkyl;
$R_3$ is hydrogen or $C_{1-6}$ alkyl; and
A is hydrogen or

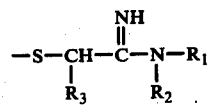

where $R_1$, $R_2$ and $R_3$ are as defined above; and pharmaceutically acceptable salts thereof.

2. A compound of claim 1 wherein the compound is N-(m-chlorophenyl)-α-mercaptoacetamidine hydrochloride.

3. The compound of claim 1 wherein the compound is N-(2,2-diphenylethyl)-2-mercaptoacetamidine hydrochloride.

4. A compound of claim 1 wherein the compound is N-(1-bicyclo-[3,3,1]nonlymethyl-2-mercaptoacetamidine.

5. A compound of claim 1 wherein the compound is N-(1,2-diphenylethyl)-α-mercaptoacetamidine hydrochloride.

6. A compound of claim 1 wherein the compound is N-cinnamyl-2-mercaptoacetamidine hydrochloride.

7. A compound of claim 1 wherein the compound is N-[1-(p-chlorophenyl)benzyl]-2-mercaptoacetamidine hydrochloride.

8. A compound of claim 1 wherein the compound is N-(1-indanyl)-2-mercaptoacetamidine hydrochloride.

* * * * *